United States Patent [19]
Rozek

[11] Patent Number: 4,782,854
[45] Date of Patent: Nov. 8, 1988

[54] ASPIRATOR SYSTEM

[75] Inventor: Roy J. Rozek, Plymouth, Wis.

[73] Assignee: Thomas Industries, Inc., Sheyboygan, Wis.

[21] Appl. No.: 48,036

[22] Filed: May 11, 1987

[51] Int. Cl.$^4$ .............................................. F16K 35/00
[52] U.S. Cl. ................... 137/315; 137/360; 137/605; 403/319; 604/119
[58] Field of Search ............ 137/605, 360, 329.1, 137/329.2, 329.3, 329.4, 356; 251/117; 604/118, 119, 249, 320; 403/315, 319

[56] References Cited

U.S. PATENT DOCUMENTS

| 1,385,178 | 7/1921 | Levedahl | 403/319 |
| 1,493,550 | 5/1924 | Keller | 403/319 |
| 1,939,509 | 12/1933 | McClelland | 137/557 X |
| 3,351,090 | 11/1967 | Brown et al. | 137/557 |
| 3,360,007 | 12/1967 | Haidek et al. | 604/118 X |
| 3,361,160 | 1/1968 | Alper | 137/557 |
| 3,441,046 | 4/1969 | Cranage | 137/329.1 |
| 3,998,227 | 12/1976 | Holbrook et al. | 604/119 |
| 4,123,089 | 10/1978 | Viero et al. | 137/329.1 X |
| 4,592,741 | 6/1986 | Vincent | 604/119 X |
| 4,606,372 | 8/1986 | Hayman | 137/315 |

Primary Examiner—Martin P. Schwadron
Assistant Examiner—Stephen M. Hepperle
Attorney, Agent, or Firm—James G. Staples

[57] ABSTRACT

The aspirator system of this invention is directed to an economical regulator assembly which can provide a substantially uniform vacuum without the need for periodic adjustment. The vacuum of the system can be easily and accurately adjusted, thereby accommodating changes in system pressure demands. The system is not prone to vacuum leakage or undesired vacuum fluctuations.

4 Claims, 1 Drawing Sheet

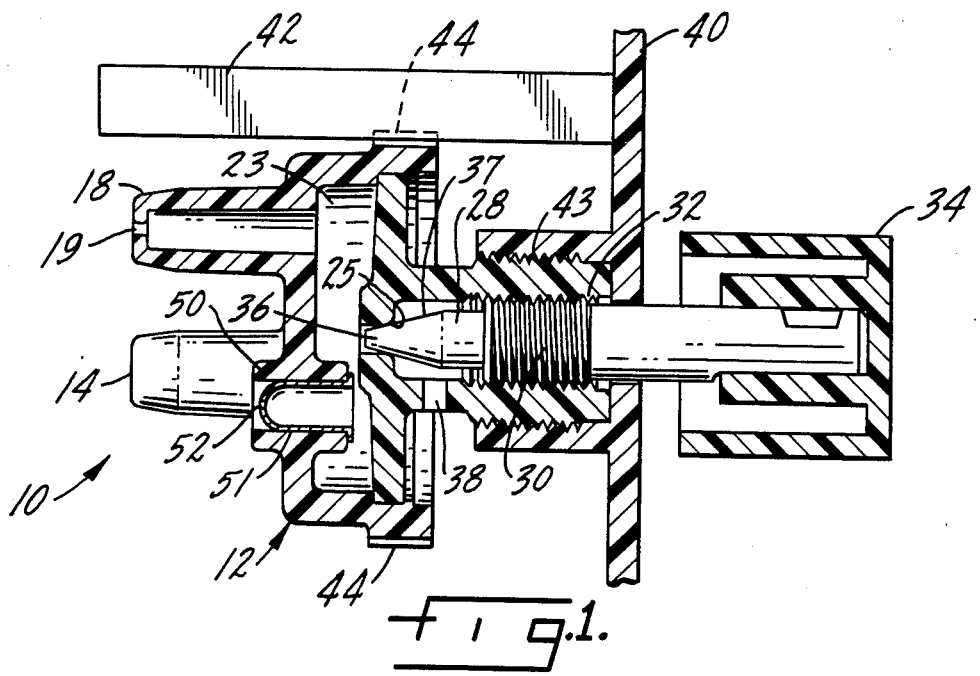
Fig. 1.
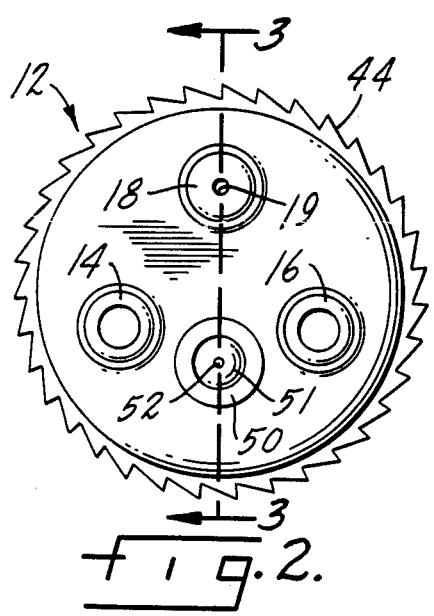
Fig. 2.
Fig. 3.

ASPIRATOR SYSTEM

FIELD OF THE INVENTION

This invention relates generally to an aspirator system. More specifically, the aspirator system of this invention is directed to an economical regulator assembly which provides a substantially uniform vacuum without the need for periodic adjustment. The vacuum level of the system can also be easily and accurately adjusted, thereby accommodating changes in system demands.

BACKGROUND OF THE INVENTION

Aspirator systems are widely used in the health care industry and this context has been chosen to illustrate the present invention. The aspirator system of this invention however can be used in numerous applications, and this invention is not meant to be confined merely to health care uses.

In typical patient care aspirator systems a lumen is inserted into a patient's lungs, surgical wound, or any area requiring the removal of fluids or suspended solids. The lumen spreads the vacuum of the system over a sufficiently wide content area to minimize tissue damage to the patient. The lumen is typically connected to a vacuum source, and the material to be removed is thereby pulled by the vacuum into the lumen, through connecting tubing, and ultimately disposed of through conventional means, such as an in-line collection receptacle.

Often the material to be removed from the patient is of a non-uniform consistency. As a result, certain portions of the material can be easily drained using a low vacuum while other portions require a higher vacuum. Aspirator systems can therefore clog as they encounter matter requiring more suction than what was previously necessary.

In this application, the term "low vacuum" will refer to an absolute pressure close to, but less than atmospheric pressure, and "high vacuum" will refer to an absolute pressure level closer to zero absolute pressure than the pressure level denominated "low vacuum."

When clogging occurs, some systems must be shut down, cleared of the obstructing material, and reactivated. Unclogging an aspirator system in this way is cumbersome, increases labor costs, and results in substantial delays. Also, some unclogging procedures can increase the risk of spreading bacteria to the patient and to the hospital environment.

One apparent solution to the clogging problem would be merely to use a higher vacuum in the system. However, such increases in vacuum must typically be controlled very carefully, because too high a vacuum may cause significant injury to the patient and damage tissue surrounding the area being suctioned. A vacuum of sufficient intensity to prevent clogging will often damage surrounding tissue once the clogging material clears the system.

Another solution would be to increase the vacuum only so long as is necessary to unclog the system, and then reduce the vacuum to normal operation. However, many conventional systems cannot be accurately controlled to increase and decrease vacuum on a demand basis.

In some conventional systems, vibration and normal handling can cause vacuum fluctuations. Also, many conventional systems are unable to maintain a steady vacuum over extended periods of time. Such systems require additional monitoring to prevent the originally set vacuum from straying to an unacceptable level, higher or lower. Some conventional systems leak vacuum at different rates under different conditions and are therefore unreliable.

Also, some systems do not accurately monitor the system vacuum, and therefore the operator may not know whether or not the appropriate vacuum is being applied. Although some systems are able to accurately control and monitor the vacuum, such systems are often very expensive. Health care costs in general are increasing, and consequently cost effective alternatives to expensive health care procedures and devices are becoming more important as time goes on.

And finally, conventional systems do not include means which operate automatically in response to attainment of an undesirable vacuum level to prevent vacuum build-up past a fixed level. If, for example, a system malfunctions to the point where the vacuum level is too high, damage to a hydrophobic filter used in the aspirator system, as well as tissue damage, can result. Thus, the existence of an undesirably high vacuum could cause a filter in the hydrophobic filter to tear, or contaminants might be sucked through the filter membrane.

Accordingly, it is an object of this invention to provide an inexpensive aspirator system wherein the system vacuum can be accurately controlled.

A further object of this invention is to provide an aspirator system in which the vacuum ca be easily maintained at a vacuum level which will not harm the patient.

A further object of this invention is to create an aspirator system which can be quickly and easily adjusted by an operator to increase the vacuum just enough to unclog the system and thereafter to quickly return the system to a "just sufficient" vacuum level.

A further object of this invention is to provide an aspirator system which provides a steady vacuum over time without the need for periodic adjustment.

Yet another object of this invention is to provide mean of limiting the maximum vacuum level that can be administered by means of appropriate vacuum relief orifices.

A further object of this invention is to provide an aspirator system which is effective, durable, inexpensive, and easy to manufacture and repair.

Other objects and features of the invention will become apparent to those skilled in the art from the following specification when read in the light of the annexed drawings.

SUMMARY OF THE INVENTION

The reliable and economical aspirator system of this invention includes a regulator assembly which provides a substantially uniform vacuum without the need for periodic adjustment. The system is not prone to vacuum leakage and can be easily and accurately adjusted to accommodate changes in system demands.

DESCRIPTION OF THE DRAWINGS

The invention is illustrated more or less diagrammatically in the accompanying drawings wherein:

FIG. 1 is a side view in cross section of the preferred embodiment;

FIG. 2 is a front view of the regulator manifold of the preferred embodiment; and FIG. 3 is a view substantially along the line 3—3 shown in FIG. 2.

DESCRIPTION OF A SPECIFIC EMBODIMENT

Like reference numbers will be used to refer to like parts from Figure to Figure in the following description of a specific embodiment of the invention.

The aspirator system of t is invention is indicated generally at 10 in FIG. 1. The regulator manifold 12 includes a vacuum inlet port 14, a vacuum outlet port 16 (see FIG. 2) and a vacuum pressure gauge port 18. In use, the inlet port 14 is connected to a typical collection device, such as a jar, by conventional tubing which in turn is connected to a lumen, and the outlet port is connected to a vacuum source by conventional tubing. The two ports are in communication with one another through chamber 23. Consequently, when a vacuum is generated by a source, the vacuum is transmitted through the outlet port, into chamber 23, through inlet port 14, and continues to the effluent collection device. Various port arrangements of collection devices are designed to allow effluents to be trapped in the collection device, and to prevent the effluent from continuing on to the regulator and vacuum source. The regulator and the vacuum source may also be protected from the suctioned material by other conventional means, i.e. by use of hydrophobic filter(s) or multiple collection jars within the effluent line. A lumen is connected to the collection device by means of conventional tubing. Therefore, when a vacuum is created, this vacuum is conveyed to the lumen, allowing suctioned effluents to be deposited within the collection device.

Pressure gauge port 18 is connected to a conventional pressure gauge with conventional tubing. The port may have a small orifice 19 shown only in FIG. 1, this orifice acting as a snubber to reduce or dampen vacuum fluctuations in the system. This dampening allows for an accurate and steady vacuum gauge reading during steady state vacuum operation. The snubber orifice, though not essential, has been found to significantly improve performance of the pressure gauge by creating accurate and reliable vacuum level readings.

Manifold 12 is sonically welded as at 22 to regulator body 20. Sonic welding creates a reliable and secure connection and typically will not leak vacuum or weaken, even in the presence of normal system vibrations, operator handling or changes in atmospheric conditions, i.e., changes in humidity, temperature, sunlight intensity, etc.

The manifold and regulator body combination forms chamber 23 which links the outlet port to the inlet port. The chamber also communicates with a pressure regulating port 24 through passage 26. The size of the passage is controlled by means of a regulator screw 28. Regulator screw 28 has screw threads 30 which engage internal compatible threads 32 of regulator body 20. An operator can screw or unscrew the regulator screw by means of knob 34 which is mechanically connected to regulator screw 28 as illustrated in FIG. 1.

As the regulator screw is moved toward the pressure regulating port 24, regulator screw point 36 moves into the mouth 25 of passage 26 which functions as a valve seat. Regulator screw point 36 has a gradually increasing diameter as illustrated at 37 in FIG. 1. Consequently, movement of regulator screw 34 into port 24 gradually decreases the passage between chamber 23 and pressure regulating port 24. As the regulator screw is screwed into port 24, it will ultimately seat the screw point 36 against the edge of passage 26, thereby closing off communication between chamber 23 and port 24.

During use, when the screw point 36 is seated against the edge of valve seat opening 26, full vacuum is applied to the lumen. However, as the regulator screw 34 moves to the right, the screw point 36 pulls away from the opening 26, and the vacuum level is then altered, because the system vacuum is decreased by air flowing into chamber 23 from port 24. This air flows from the surrounding ambient atmosphere through aperture 38 in regulator body 20 and into port 24. Consequently, port 24 remains essentially at atmospheric pressure, and the system's vacuum decreases in proportion to the distance regulator screw point 37 is moved away from opening 26. The degree of vacuum to the lumen can therefore be accurately controlled by the screw thread controlled engagement of the regulator screw 28 in relation to the mouth of passage 26 of port 24.

The vacuum level within chamber 23 is also controlled by means of a small relief orifice 52. This orifice may be located on a separate component such as the thimble-like relief tube 51 shown within boss 50. Other locations for this orifice may be as part of the manifold itself or as a properly sized notch on the screw point 37.

The position of regulator manifold 12 and regulator body 20 is adjusted with respect to shroud 40 by means of screw threads 43. Shroud 40 has a flexible tab 42 which locks into rachet teeth 44 located along the peripheral surface of manifold 12, as illustrated in FIG. 2. As the manifold and regulator body move clockwise into the shroud, tab 42 moves up the incline of each ratchet tooth, and falls down into the following notch, continuing in similar manner until clockwise rotational tightening is complete Thereafter, the tab locks up the system because the abutment surface of each ratchet tooth impedes counterclockwise or loosening rotational movement of the manifold relative to the shroud. As a result, the tab locks the ratchet teeth in place and thereby prevents the manifold from loosening. Before the manifold and regulator body can be loosened or disengaged from the shroud, the operator must first bend tab 42 away from ratchet teeth 44; this allows counterclockwise rotation of the manifold. The tab locking system dramatically increases reliability without substantially increasing overall cost.

In use, the aspirator system of this invention is very accurate and reliable. The snubber 19 which dampens vacuum fluctuations and results in accurate pressure gauge readings. The sonically welded construction, as discussed above, creates a sturdy apparatus which will prevent undesirable leakage under normal conditions. The relief tube 51 and relief orifice 38 can be incorporated to provide a controlled reduction of the maximum vacuum level.

The regulator screw can quickly and easily be screwed or unscrewed to alter the vacuum as required. The system can be accurately adjusted by means of the regulator screw to create the lowest vacuum possible for removing solid material. Once the system clogs, the regulator screw can be adjusted to quickly increase the vacuum level, thereby unclogging the system; thereafter, the pressure can be quickly reduced to the original level. The system therefore efficiently removes material at the lowest vacuum possible and for only the briefest time necessary, thereby minimizing damage to the patient during use.

It should be understood that the foregoing disclosure is intended to be exemplary only and that numerous modifications or alterations may be made therein without departing from the spirit and scope of the invention as set forth in the appended claims.

I claim:

1. A manual mechanically lockable regulator valve assembly for an aspirator system, said regulator valve assembly including a manifold housing which forms a manifold, said manifold housing having a generally circular peripheral portion, means carried by the manifold housing for supporting said manifold housing from a base structure comprising cooperating thread means on the housing and the base structure to thereby provide rotary coupling motion between the manifold housing and the support base, a pressure regulation inlet in the manifold in communication with a source of vacuum, a pressure regulation outlet in the manifold adapted for communication with a space to be evacuated, a pressure regulation port in the manifold housing which connects the manifold to the atmosphere, a pressure regulator associated with the pressure regulation port for varying the size of the pressure regulation port and thereby the absolute pressure in the manifold, said pressure regulator being movable from a fully opened position in which it enables atmospheric pressure to be established in the manifold to a fully closed position in which it closes off communication between the manifold and the atmosphere through the pressure regulation port to thereby enabled a less than atmospheric pressure to be established, and mechanical locking means for positively mechanically locking the manifold housing and pressure regulator into a fixed position said mechanical locking means including a plurality of ratchet teeth and a ratchet member, said ratchet teeth and being carried by the base structure said ratchet member engaging said ratchet teeth, said ratchet teeth and ratchet member thereby precluding rotary movement of the manifold with respect to said base structure until said ratchet teeth and ratchet member are manually operated to override the mechanical lock formed by the ratchet teeth and ratchet member, thus permitting rotary uncoupling motion.

2. The manually mechanically lockable regulator valve assembly of claim 1 further characterized firstly, in that the plurality of ratchet teeth are carried by the said circular peripheral portion of the manifold housing, and secondly, in that the ratchet member projects from and is carried by said base structure.

3. The manually mechanically lockable regulator valve assembly of either claim 1 or claim 2 further characterized by and including means for changing the location of the pressure regulator, and thereby the size of the pressure regulating port and the absolute pressure in the manifold, while the ratchet teeth and ratchet member maintain the manifold in a fixed position with respect to said base structure.

4. A manually mechanically lockable regulator valve assembly for an aspirator system, said regulator valve assembly including a manifold housing which forms a manifold, said manifold housing having a generally circular peripheral portion, means carried by the manifold housing for supporting said manifold housing from a base structure, a pressure regulation inlet in the manifold in communication with a source of vacuum, a pressure regulation outlet in the manifold adapted for communication with a space to be evacuated, a pressure regulation port in the manifold adapted for connects the manifold to the atmosphere, a pressure regulator associated with the pressure regulation port for varying the size of the pressure regulation port and thereby the absolute pressure in the manifold, said pressure regulator being movable from a fully opened position in which it enables atmospheric pressure to be established in the manifold to a fully closed position in which it closes off communication between the manifold and the atmosphere through the pressure regulator port, and mechanical locking means for postively mechanically locking the manifold housing and pressure regulator into a fixed position, said mechanical locking means including a plurality of ratchet teeth and a ratchet member, said ratchet member being carried by the base structure, the plurality of ratchet member being carried by the said circular peripheral portion of the manifold housing, and the ratchet member projecting from and being carried by said base structure, said ratchet being integrally formed with the base structure and the manifold housing, said ratchet member engaging said ratchet teeth, said ratchet teeth and ratchet member thereby precluding movement of the manifold with respect to said base structure until said ratchet teeth and ratchet member are manually operated to override the mechanical lock formed by the ratchet teeth and ratchet member.

* * * * *